United States Patent
Kim et al.

(10) Patent No.: US 10,066,391 B2
(45) Date of Patent: Sep. 4, 2018

(54) FLOOR COVERING HAVING ADJUSTABLE HARDNESS

(71) Applicant: INTERNATIONAL BUSINESS MACHINES CORPORATION, Armonk, NY (US)

(72) Inventors: Minkyong Kim, Scarsdale, NY (US); Min Li, San Jose, CA (US); Clifford A. Pickover, Yorktown Heights, NY (US); Valentina Salapura, Chappaqua, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 14/967,409

(22) Filed: Dec. 14, 2015

(65) Prior Publication Data
US 2016/0370271 A1 Dec. 22, 2016

Related U.S. Application Data

(63) Continuation of application No. 14/744,417, filed on Jun. 19, 2015.

(51) Int. Cl.
| | | |
|---|---|---|
| *E04H 9/00* | (2006.01) | |
| *E04B 5/43* | (2006.01) | |
| *G01N 3/40* | (2006.01) | |
| *E04F 15/00* | (2006.01) | |

(52) U.S. Cl.
CPC ............... *E04B 5/43* (2013.01); *E04F 15/00* (2013.01); *G01N 3/40* (2013.01)

(58) Field of Classification Search
CPC .............. G01N 3/40; E04F 15/00; E04B 5/43

USPC .................................................. 52/1
See application file for complete search history.

(56) References Cited

U.S. PATENT DOCUMENTS

| | | | | |
|---|---|---|---|---|
| 3,287,203 A | * | 11/1966 | Elmendorf | E04F 15/022 428/167 |
| 5,068,018 A | * | 11/1991 | Carlson | G05B 19/02 188/267.1 |
| 2005/0151350 A1 | * | 7/2005 | Watson | A63C 5/07 280/602 |
| 2006/0099808 A1 | * | 5/2006 | Kondo | F16F 9/532 438/674 |
| 2006/0248750 A1 | * | 11/2006 | Rosenberg | A43B 1/0054 36/29 |
| 2010/0099507 A1 | * | 4/2010 | Gregersen | A63C 19/04 472/92 |

(Continued)

OTHER PUBLICATIONS

Kim et al., "Floor Covering Having Adjustable Hardness" U.S. Appl. No. 17/744,417, filed Jun. 19, 2015.

(Continued)

*Primary Examiner* — Brain E Glessner
*Assistant Examiner* — Joshua K Ihezie
(74) *Attorney, Agent, or Firm* — Cantor Colburn LLP; Rahan Uddin

(57) ABSTRACT

Embodiments include method, systems and computer program products for adjusting a hardness of a floor covering. Aspects include monitoring a user on the floor covering and detecting a triggering event associated with the user. Aspects also include adjusting a parameter of the floor covering, wherein the adjustment decreases the hardness of the floor covering.

6 Claims, 5 Drawing Sheets

(56) References Cited

U.S. PATENT DOCUMENTS

2012/0123190 A1* 5/2012 Majidi .................... F16F 9/535
  600/15
2015/0175236 A1* 6/2015 Walthert ................ B62K 25/04
  280/5.515

OTHER PUBLICATIONS

List of IBM Patents or Patent Applications Treated as Related-Date Filed: Feb. 29, 2016; 2 pages.

* cited by examiner

FLOOR COVERING HAVING ADJUSTABLE HARDNESS

DOMESTIC PRIORITY

This application is a continuation of U.S. patent application Ser. No. 14/744,417, filed Jun. 19, 2015, the disclosure of which is incorporated by reference herein in its entirety.

BACKGROUND

The present disclosure relates to a floor covering having an adjustable hardness, and more specifically, to methods, systems and computer program products for adjusting the hardness of a floor covering.

As the population ages and people live longer in poor physical shape, the number of people who fall and suffer serious, even fatal, injuries is increasing at a high rate. In the United States alone, the number of people over 65 who died after a fall reached nearly 24,000 in 2012. Unfortunately, preventing a fall, and the resulting injuries, is not simply a matter of training individuals to be more careful.

SUMMARY

In accordance with an embodiment, a method for adjusting the hardness of a floor covering based on the detection of a triggering event is provided. The method includes monitoring a user on the floor covering and detecting a triggering event associated with the user. The method also includes adjusting a parameter of the floor covering, wherein the adjustment decreases the hardness of the floor covering.

In accordance with another embodiment, a system for adjusting the hardness of a floor covering based on the detection of a triggering event includes a processor and a user interface, the processor being configured to perform a method. The method includes monitoring a user on the floor covering and detecting a triggering event associated with the user. The method also includes adjusting a parameter of the floor covering, wherein the adjustment decreases the hardness of the floor covering.

In accordance with a further embodiment, a computer program product for adjusting the hardness of a floor covering based on the detection of a triggering event includes a non-transitory storage medium readable by a processing circuit and storing instructions for execution by the processing circuit for performing a method. The method includes monitoring a user on the floor covering and detecting a triggering event associated with the user. The method also includes adjusting a parameter of the floor covering, wherein the adjustment decreases the hardness of the floor covering.

BRIEF DESCRIPTION OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

In accordance with exemplary embodiments of the disclosure, methods, systems and computer program products for adjusting the hardness of a floor covering based on the detection of a triggering event are provided. In exemplary embodiments, a floor covering having an adjustable hardness is used to soften the impact that and user experiences when falling on the floor covering. The floor covering may be a carpet or mat designed to be placed on an existing floor or it may be part of a flooring system, such as a hardwood floor, a linoleum floor or engineered hardwood floor. In exemplary embodiments, a triggering event, such as a user slipping or falling, is detected by one or more sensors and the hardness of the floor covering is adjusted to decrease the hardness of the floor to soften the impact of the user with the floor covering. In exemplary embodiments, the user of the floor covering may be a person (including adults, children and infants), a pet, or anything else known in the art.

Figure 1:
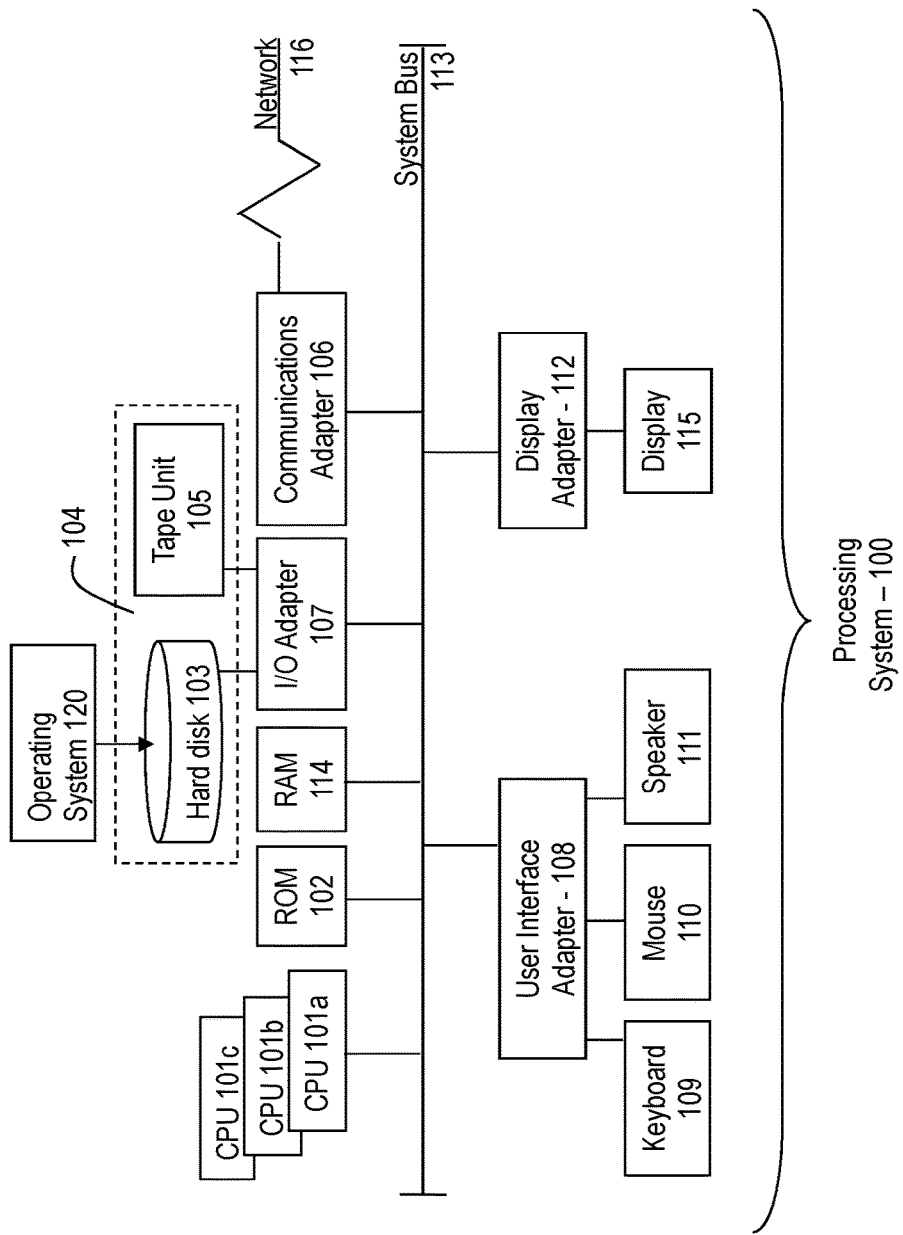
FIG. 1 is a block diagram illustrating one example of a processing system for practice of the teachings herein.

Referring to FIG. 1, there is shown an embodiment of a processing system 100 for implementing the teachings herein. In this embodiment, the system 100 has one or more central processing units (processors) 101a, 101b, 101c, etc. (collectively or generically referred to as processor(s) 101). In one embodiment, each processor 101 may include a reduced instruction set computer (RISC) microprocessor. Processors 101 are coupled to system memory 114 and various other components via a system bus 113. Read only memory (ROM) 102 is coupled to the system bus 113 and may include a basic input/output system (BIOS), which controls certain basic functions of system 100.

FIG. 1 further depicts an input/output (I/O) adapter 107 and a network adapter 106 coupled to the system bus 113. I/O adapter 107 may be a small computer system interface (SCSI) adapter that communicates with a hard disk 103 and/or tape storage drive 105 or any other similar component. I/O adapter 107, hard disk 103, and tape storage device 105 are collectively referred to herein as mass storage 104. Operating system 120 for execution on the processing system 100 may be stored in mass storage 104. A network adapter 106 interconnects bus 113 with an outside network 116 enabling data processing system 100 to communicate with other such systems. A screen (e.g., a display monitor) 115 is connected to system bus 113 by display adaptor 112, which may include a graphics adapter to improve the performance of graphics intensive applications and a video controller. In one embodiment, adapters 107, 106, and 112 may be connected to one or more I/O busses that are connected to system bus 113 via an intermediate bus bridge (not shown). Suitable I/O buses for connecting peripheral devices such as hard disk controllers, network adapters, and graphics adapters typically include common protocols, such as the Peripheral Component Interconnect (PCI). Additional input/output devices are shown as connected to system bus 113 via user interface adapter 108 and display adapter 112.

A keyboard 109, mouse 110, and speaker 111 all interconnected to bus 113 via user interface adapter 108, which may include, for example, a Super I/O chip integrating multiple device adapters into a single integrated circuit.

Thus, as configured in FIG. 1, the system 100 includes processing capability in the form of processors 101, storage capability including system memory 114 and mass storage 104, input means such as keyboard 109 and mouse 110, and output capability including speaker 111 and display 115. In one embodiment, a portion of system memory 114 and mass storage 104 collectively store an operating system such as the AIX® operating system from IBM Corporation to coordinate the functions of the various components shown in FIG. 1.

Figure 2A:
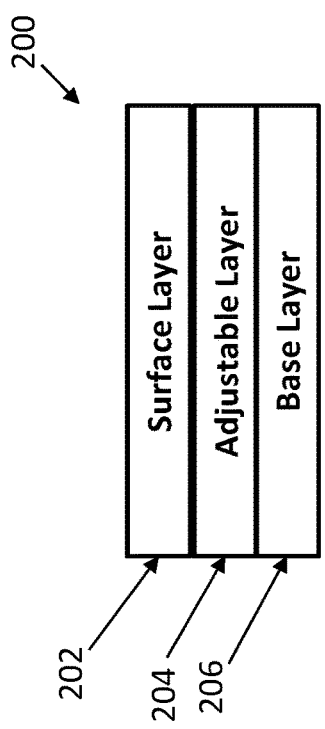
FIGS. 2A and 2B are block diagrams illustrating floor coverings having an adjustable hardness in accordance with exemplary embodiments.

Referring now to FIG. 2A, a block diagram illustrating a floor covering 200 having an adjustable hardness in accordance with an embodiment is shown. The floor covering 200 may be a carpet or mat designed to be placed on an existing floor or it may be part of a flooring system, such as a hardwood floor, a linoleum floor or engineered hardwood floor. In exemplary embodiments, the floor covering 200 includes a surface layer 202, an adjustable layer 204 and a base layer 206. In exemplary embodiments, the surface layer 202 may be the top layer of the floor covering 200 and may include hardwood, carpet, linoleum, engineered hardwood, or any other suitable material. In one embodiment, the base layer 206 is formed from a rigid material such a plywood, oriented strand board (OSB), metal, or the like. The adjustable layer 204 couples the surface layer 202 to the base layer 206 and is configured to have an adjustable parameter that can be used to adjust the amount that the surface layer 202 can move towards the base layer 206.

In exemplary embodiments, the adjustable layer 204 may include a layer of magnetorheological (MR) fluid or electrorheological (ER) fluid. In these embodiments, the viscosity of the MR/IR fluid can be controlled to effectively adjust the hardness of the floor covering 200. For example, when the MR/IR fluid is configured to have a high viscosity the hardness of the floor covering 200 will be high because the fluid will not be allowed to move within the adjustable layer 204 and thus the surface layer 202 will not be allowed to move towards the base layer 206 upon an impact to the surface layer 202. In contrast, when the MR/IR fluid is configured to have a low viscosity the hardness of the floor covering 200 will be low because the fluid will be able to move within the adjustable layer 204 and thus the surface layer 202 will be allowed to move towards the base layer 206 upon an impact to the surface layer 202.

Figure 2B:
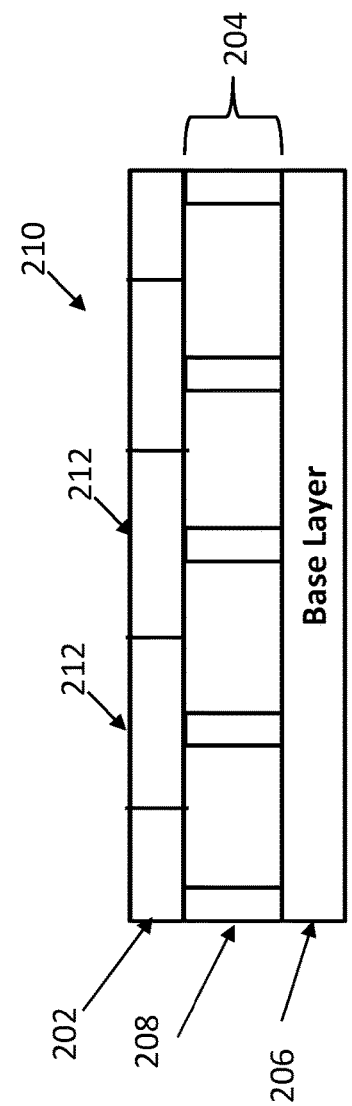

Referring now to FIG. 2B, a block diagram illustrating a floor covering 200 having an adjustable hardness in accordance with another embodiment is shown. In exemplary embodiments, the floor covering 200 includes a surface layer 202, an adjustable layer 204 and a base layer 206. In exemplary embodiments, the surface layer 202 may be the top layer of the floor covering 200 and may include a plurality of regions 212. The regions 212 may be made of hardwood, carpet, linoleum, engineered hardwood, or any other suitable material. In one embodiment, the base layer 206 is formed from a rigid material such a plywood, oriented strand board (OSB), metal, or the like. The adjustable layer 204 includes a plurality of coupling devices 208 that couple regions 212 of the surface layer 202 to the base layer 206 and that are configured to have an adjustable parameter that can be used to adjust the amount that the surface layer 202 can move towards the base layer 206.

In exemplary embodiments, each of the regions 212 of the surface layer 202 are coupled to the base layer 206 by one or more coupling devices 208 that can be independently controlled. In exemplary embodiments, the coupling devices 208 may be variable stiffness actuators, IR/MR dampers or the like. In exemplary embodiments, the number and size of the regions 212 in the surface layer 202 may be selected based on the expected usage of the floor covering 200. In addition, the number of the coupling devices 208 that are coupled to each of the regions 212 can be selected based on the expected usage of the floor covering 200. In exemplary embodiments, the hardness of the regions 212 of the floor covering 200 may be adjusted by selectively controlling the one or more coupling devices 208 for each region. The coupling devices 208 coupled to each region 212 may be configured to be controlled as a group or independently to allow fine tuning of the hardness for the region.

Figure 3:
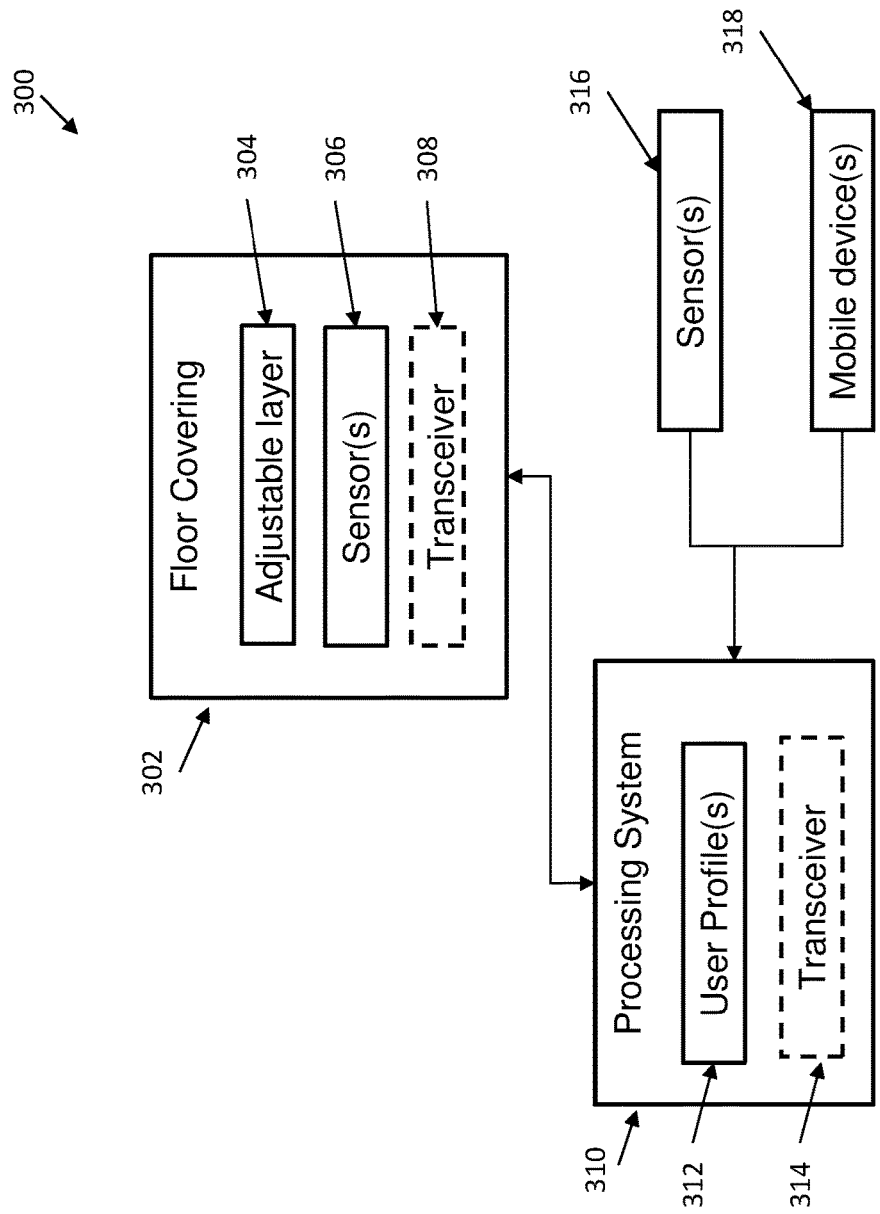
FIG. 3 is a block diagram illustrating a system for adjusting the hardness of a floor covering based on the detection of a triggering event in accordance with an exemplary embodiment.

Referring now to FIG. 3, a block diagram illustrating a system 300 for adjusting the hardness of a floor covering 302 based on the detection of a triggering event in accordance with an exemplary embodiment is shown. As illustrated, the system 300 includes a floor covering 302 that includes an adjustable layer 304 and one or more sensors 306. The sensors 306 may be pressure sensors disposed at various locations in the floor covering 302 that can be used to detect the presence of a user on the floor covering 302, the location of a user on the floor covering 302, and in some embodiments that the user on the floor covering 302 has slipped or is in the process of falling. The system 300 also includes a processing system 310, which may be similar to the one shown in FIG. 1, which is configured to communicate with the floor covering 302 via transceivers 308, 314. In various embodiments, the processing system 310 may be physical connected to the floor covering 302 or it may communicate with the floor covering 302 wirelessly.

In exemplary embodiments, the processing system 310 may receive data from a variety of sources including from the sensors 306 disposed within or on the floor covering 302, from one or more sensors 316 that are external to the floor covering 302, and/or from a mobile device 318. In exemplary embodiments, the sensors 316 may include, but are not limited to, accelerometers, video capture devices, a PIR (passive infrared) detection unit view, or the like. In exemplary embodiments, the mobile device 318 may be a smartphone having a falling detection application or any other suitable wearable device having suitable sensors and a falling detection application.

In exemplary embodiments, the processing system 310 is configured to detect a triggering event, which may be an event that indicates that a user on the floor covering 302 is in the process of falling. In exemplary embodiments, fall detection may involve monitoring of human body posture change by an acceleration sensor and a tilt angle sensor. In one embodiment, the processing system 310 may include falling detection software that is configured to monitor people in the area of the floor covering 302 for abnormal behavior that typically happens prior to a user falling. In exemplary embodiments, the software may detect that a person is about to fall by measuring their body posture and then extracting multiple characteristic quantities from the human body posture. These characteristics can be acquired in real time and be input into the falling detection software for detection. The falling detection software may use a classifier that has been trained with multiple parameters and that has weighting coefficient for each of the parameters to calculate a risk, or confidence level C, that the person is about to fall. The confidence level C of an impending fall may be estimated in real-time, and if the level of C is above a threshold value, the floor covering 302 may be adjusted. In exemplary embodiments, the threshold confidence level for adjusting the floor covering 302 may be set by the person, caregiver, and/or it may be learned by the falling detection application and involve machine learning.

Figure 4:
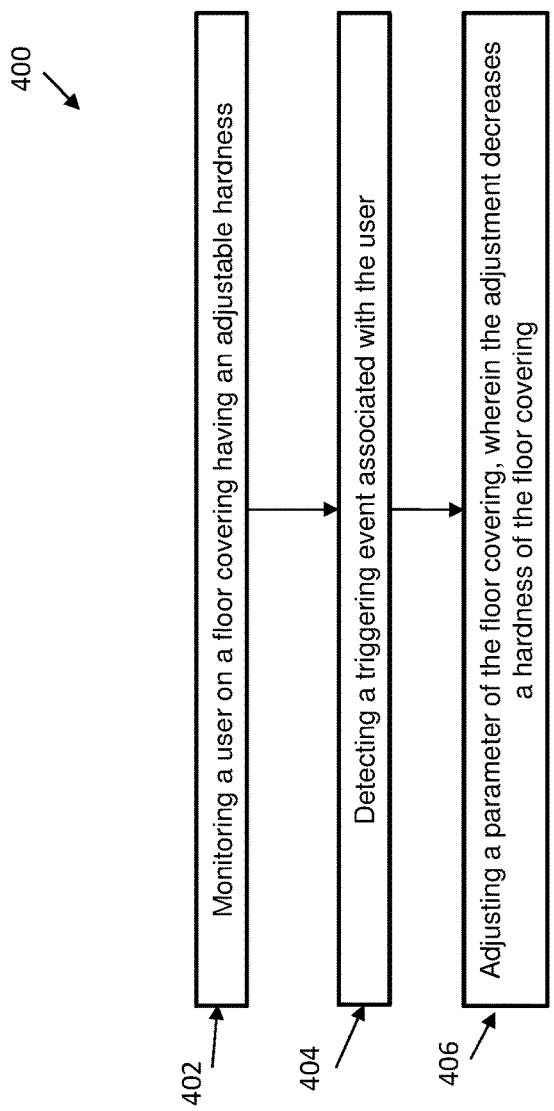
FIG. 4 is a flow diagram of a method for adjusting the hardness of a floor covering based on the detection of a triggering event in accordance with an exemplary embodiment.

Referring now to FIG. 4, a flow diagram of a method 400 for adjusting the hardness of a floor covering based on the detection of a triggering event in accordance with an exemplary embodiment is shown. As shown at block 402, the method 400 includes monitoring a user on a floor covering having an adjustable hardness. In exemplary embodiments, monitoring the user on the floor covering may include monitoring a location of a person and/or monitoring the gait of the person. In addition, monitoring the user on the floor covering may include communicating with an electronic device associated with the user, such as a smartphone in the user's possession, to obtain information, including the identity of the user. Next, as shown at block 404, the method 400 includes detecting a triggering event associated with the user. In exemplary embodiments, the triggering event may be an event that indicates that the user is falling or about to fall. Many existing techniques for detecting that a user is falling are well known in the art and any suitable technique can be used. Next, as shown at block 406, the method 400 includes adjusting a parameter of the floor covering, wherein the adjustment decreases a hardness of the floor covering. In exemplary embodiments, the parameter may be a viscosity of an IR/MR fluid disposed within the floor covering. In exemplary embodiments, the adjustment may be made across the entire floor covering or it may be made in only in an area within a predetermined distance of the location of the user. The size of the area may be static or it may be based on the identity of the person, the weight or the person, a direction of travel of the person, or the like.

Figure 5:
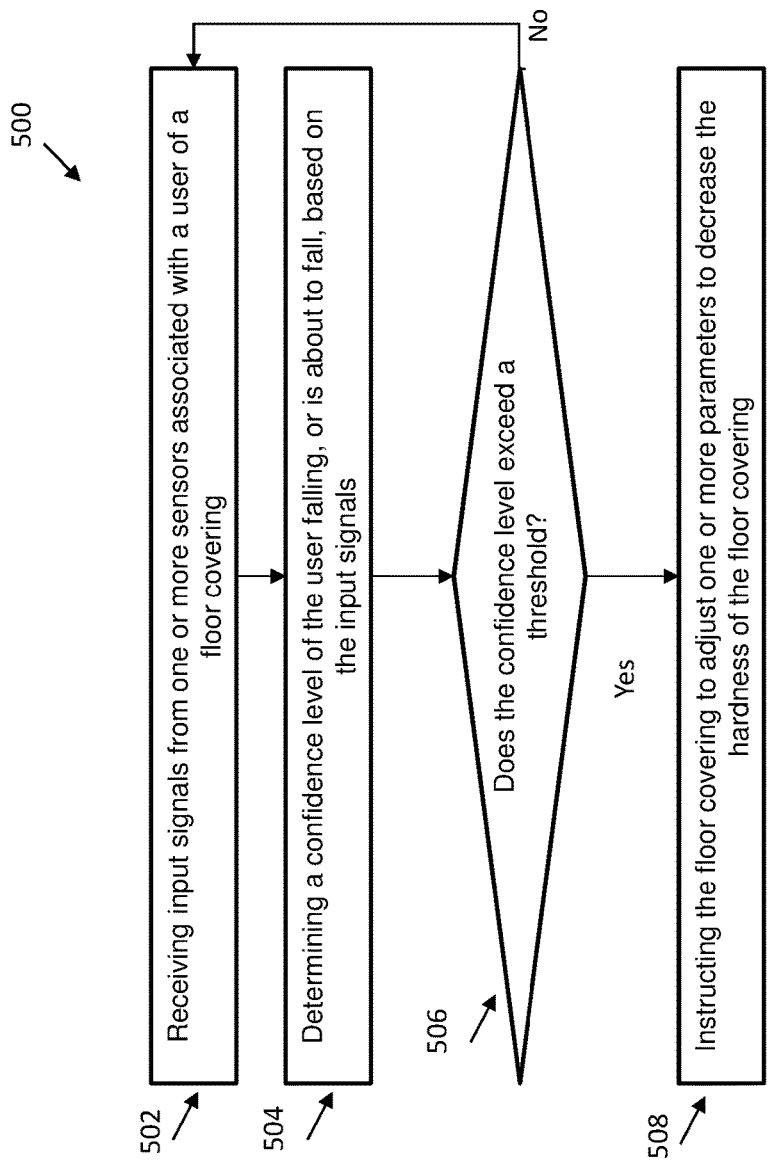
FIG. 5 is a flow diagram of a method for adjusting the hardness of a floor covering in accordance with an exemplary embodiment.

Referring now to FIG. 5, a flow diagram of a method 500 for adjusting the hardness of a floor covering in accordance with an exemplary embodiment is shown. As shown at block 502, the method 500 includes receiving input signals from one or more sensors associated with a user on a floor covering. In an exemplary embodiment, the input signals may include signals from pressure sensors in the floor covering, signals from accelerometers disposed on the person (such as on a smartwatch or within a smartphone in the person's pocket or hand), signals from a camera monitoring the user, or the like. Next, as shown at block 504, the method 500 includes determining a confidence level that the user falling, or is about to fall, based on the input signals. In exemplary embodiments, the calculation of the confidence level may also be based on an identity or characteristic (weight, gait, etc.) of the person.

As shown at decision block 506, the method 500 also includes determining if the confidence level exceeds a threshold. In exemplary embodiments, the threshold may be based on an identity or characteristic (weight, gait, etc.) of the person. If the confidence level exceeds the threshold, the method 500 proceeds to block 508 and includes instructing the floor covering to adjust one or more parameters to decrease the hardness of the floor covering. In exemplary embodiments, the parameter may be a viscosity of an IR/MR fluid disposed within the floor covering. In exemplary embodiments, the adjustment may be made across the entire floor covering or it may be made in only in an area within a predetermined distance of the location of the person. The size of the area may be static or it may be based on the identity of the person, the weight or the person, a direction of travel of the person, or the like.

In exemplary embodiments, the processing system may be configured to identify people at a high-risk of falling and may lower the threshold used for determining when to make adjustments to the floor covering. Likewise, the calculation of the confidence level may also be modified based on knowledge of the person, including an individual risk factor. In exemplary embodiment, the processing system 310 may store individual profiles 312 that include cognitive or health information for persons on the floor covering. In such systems, the decision to adjust the hardness of the floor covering may also be based on information stored in the individual profile 312, which may include various information including cognitive/health state (e.g., pre-Alzheimer's, Parkinson's, autism, motor-control characteristics, etc.). In exemplary embodiments, certain motor-control characteristics of persons on the floor covering may be inferred by a monitoring of a person's history of falls, or near-falls. Likewise, the system may monitor a characteristic of the person, such as the gait of the person, to sensing if the person is elderly or has an impaired mobility or walking capability by analyzing the step width and pattern. In exemplary embodiments, the risk of a person on the floor covering falling may be based on a cognitive state of the person. For example, individuals with impaired cognitive states, such as nausea, drowsiness, a drunken condition, and extreme stress level may place a healthy person at an elevated risk of falling.

In one embodiment, a camera and/or sensor may detect the presence of a toddler or a baby on the floor. Accordingly, if a baby that is learning to walk is located in certain area on the floor, that area may have a reduced threshold for determining if the person is falling and/or a pre-set confidence level C of an impending fall can be increased. In another embodiment, the floor covering may be used on playgrounds, where children, particularly small children, are playing. The flooring under monkey bars, swings and similar play sets, where children's falls are more likely can be pre-set to higher sensitivity level. In a further embodiment, the floor covering may be used in hospital rooms of sick and after-surgery patients who are recovering, and starting to move by themselves. The area of the floor around restroom and between bed and restroom is may be pre-set to higher sensitivity level when it is detected that feet touch the floor and the patient starts to move. In exemplary embodiments, floor coverings having adjustable hardness may also be used for on-the-fly creation of a yoga mat on floor, on-the-fly creation of a sleeping surface on the floor. In yet another embodiment, when the floor covering detects that an actual fall has occurred, the processing system may be configured to create an alert requesting medical assistance for the person.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method for adjusting a hardness of a floor covering, the method comprising:
   monitoring a user on the floor covering using one or more sensors disposed within the floor covering;
   detecting a triggering event associated with the user;
   adjusting a parameter of the floor covering, wherein the adjustment decreases the hardness of the floor covering, wherein the floor covering is a permanent flooring system that consists of one of a hardwood floor, a linoleum floor and an engineered hardwood floor.

2. The method of claim 1, wherein the parameter of the floor covering is a viscosity of a magnetorheological fluid or electrorheological fluid disposed within the floor covering.

3. The method of claim 1, wherein monitoring the user on the floor covering further comprises using one or more sensors that are disposed on the user.

4. The method of claim 1, wherein the detection of a triggering event includes calculating a risk that the user is about to fall by monitoring a characteristic of the user and determining if the risk exceeds a threshold value.

5. The method of claim 4, wherein at least one of the risk and the threshold value are based on an individual profile of the user.

6. The method of claim 4, wherein at least one of the risk and the threshold value are based on the characteristic of the user.

* * * * *